United States Patent

Love

[11] Patent Number: 5,984,856
[45] Date of Patent: Nov. 16, 1999

[54] SPIRAL FIELD MAGNETIC PRODUCT

[75] Inventor: C. Allen Love, Marietta, Ohio

[73] Assignee: Magnum Magnetics, Marietta, Ohio

[21] Appl. No.: 09/105,998

[22] Filed: Jun. 29, 1998

[51] Int. Cl.⁶ .................................................. A61B 17/52
[52] U.S. Cl. .................................................. 600/15
[58] Field of Search .............................. 600/9–15

[56] References Cited

U.S. PATENT DOCUMENTS

| | | | |
|---|---|---|---|
| 4,022,189 | 5/1977 | Boxer | 600/15 |
| 4,162,672 | 7/1979 | Yazaki | 600/15 |
| 4,489,711 | 12/1984 | Latzke | 600/15 |
| 4,549,532 | 10/1985 | Baermann | 600/15 |
| 5,277,692 | 1/1994 | Ardizzone | 600/9 |

*Primary Examiner*—Samuel Gilbert
*Attorney, Agent, or Firm*—Vorys Sater Seymour & Pease LLP

[57] ABSTRACT

A thin, flexible magnetic sheet material for therapeutic purposes has a spiral magnetization pattern in which areas of alternating north and south magnetic polarity are arranged in a concentric spiral pattern expanding from a center point. The sheet material may incorporate an adhesive layer for fastening to the skin of a patient.

6 Claims, 3 Drawing Sheets

SPIRAL FIELD MAGNETIC PRODUCT

BACKGROUND OF THE INVENTION

1. Field of the Invention

This invention relates to magnetic sheet materials and more particularly to flexible magnetic sheet materials for therapeutic use.

2. Brief Description of the Prior Art

A number of magnetic sheet materials intended for application to the surface of a human or animal body for therapeutic effect have been devised. Mitsuno, U.S. Pat. No. 5,304,111, discloses a flexible planar magnetic sheet material for therapeutic use having areas of alternating magnetic polarity. Mitsuno discloses a pattern wherein generally circular areas of one magnetic polarity are surrounded by a general background of the opposite magnetic polarity. Mitsuno also discloses a pattern of undulating interdigitated areas of alternating magnetic polarity. Baermann, U.S. Pat. No. 4,549,532 discloses a flexible magnetic sheet for therapeutic use made of magnetic particles dispersed in a rubbery matrix and having concentric circles or rectangles of alternating magnetic polarity. In another embodiment, Baermann's magnetic sheet has sectors of alternating polarity.

The therapeutic magnetic materials of the prior art have attempted to provide a pattern of magnetic polarity that does not have a preferential orientation with respect to anatomical structures, e.g., blood vessels, in or close to the skin. Such patterns are intended to insure that the effect of the magnetic field on the anatomical structures in uniform in any direction. However, the known patterns may not provide for such uniform influence in all cases.

Accordingly a need has continued to exist for an improved therapeutic magnetic sheet material having a pattern that provides a highly symmetrical arrangement of magnetic poles.

SUMMARY OF THE INVENTION

The deficiencies of the therapeutic magnetic sheet materials of the prior art with respect to non-uniform therapeutic effect have now been alleviated by the magnetic sheet material of the invention wherein a thin, flexible sheet of magnetic material is magnetized in a spiral pattern. Areas of north and south magnetic polarity are formed in a concentric intertwined spiral pattern around a center. The material may incorporate an adhesive layer for fastening to the skin of a patient for therapeutic purposes.

Accordingly, it is an object of the invention to provide a magnetic sheet material for therapeutic use.

A further object is to provide a magnetic sheet material having a spiral magnetic pattern.

Further objects of the invention will become apparent from the description of the invention which follows.

DETAILED DESCRIPTION OF THE INVENTION AND PREFERRED EMBODIMENTS

Figure 1:
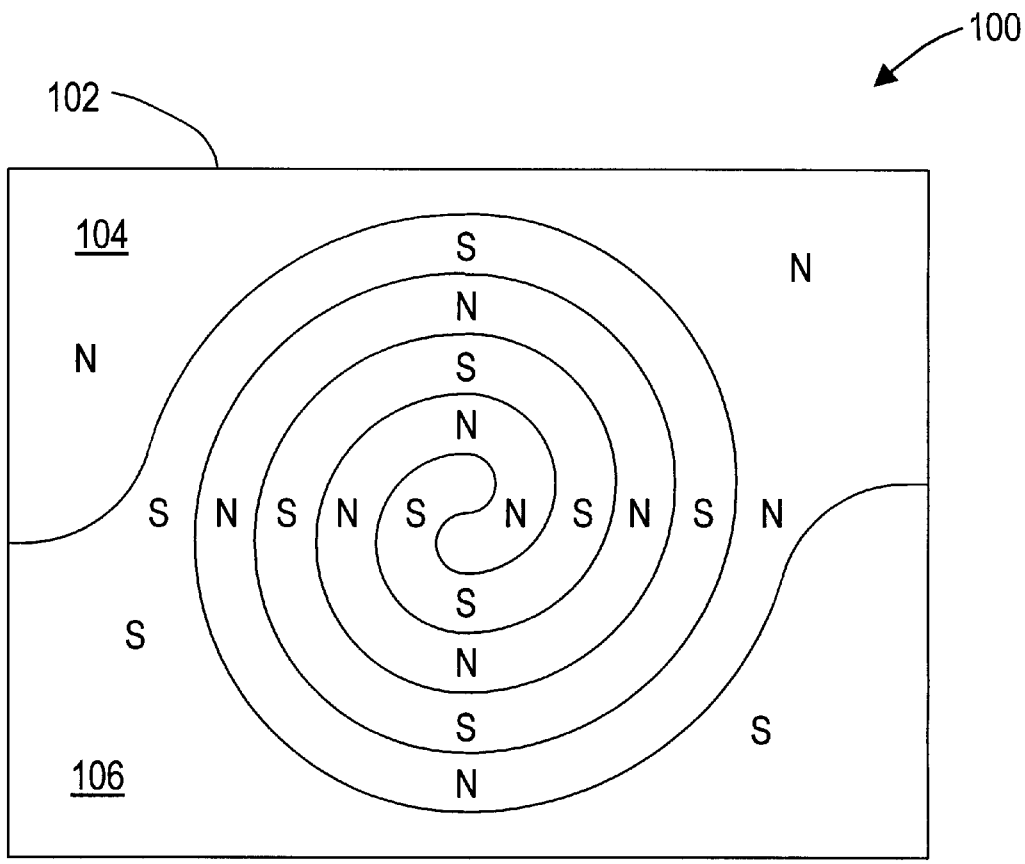
FIG. 1 illustrates a magnetic sheet article of the invention schematically showing the spiral magnetic pattern of north and south magnetic poled areas.

The magnetic sheet material of the invention provides a spiral pattern in which areas of alternating north and south magnetic polarity are arranged in a concentric spiral pattern expanding from a center point. A representative spiral pattern is shown in FIG. 1. A magnetic sheet article 100 comprises a layer of magnetic material 102 that has been poled to provide a spiral magnetic field pattern indicated by the letters N and S to indicate the regions 104 and 106 of the layer having north and south magnetic polarity respectively.

The sheet material is intended to be applied to the surface of the skin of a patient in order to exert a magnetic effect on the structures in close proximity to the skin. In particular, the magnetic field provided by the magnetic sheet material of the invention is intended to interact with the blood flowing through vessels near the skin in order to produce the therapeutic effects that have been proposed for such materials. The spiral pattern of the sheet material according to the invention provides a magnetic field of such symmetry that a material, such a blood in a vessel close to the skin, experiences a similar changing magnetic field as it traverses the sheet, no matter in which way the vessel is oriented.

The general spiral pattern as illustrated may be varied and modified in a number of ways. The radial widths of the areas of north and south polarity may vary from relatively narrow to relatively wide, depending on the intended use. Accordingly, the widths may vary from about 1.0 mm to about 30 mm in width. The radial width of the north and south poled areas may vary with the radial distance from the center of symmetry, either being narrow near the center and wider further from the center or wider near the center and narrower near the periphery. Although in a preferred embodiment the radial widths of the north and south poled areas are equal, it is not excluded that the radial width of one of the areas may be narrower than that of the other. Consequently, the exact pattern may vary in detail while retaining the general spiral pattern with radially alternating north and south poled areas.

The magnetic material carrying the spiral pattern of the invention may be any magnetizable material. It is preferred that the sheet material be flexible for ease in conforming to the human body to which it is intended to be applied. A preferred magnetic material is a dispersion of magnetizable particles in a flexible sheet of natural or synthetic resin such as rubber or synthetic resin. Such magnetic sheet materials are entirely conventional and may be prepared by conventional techniques.

Figure 2:
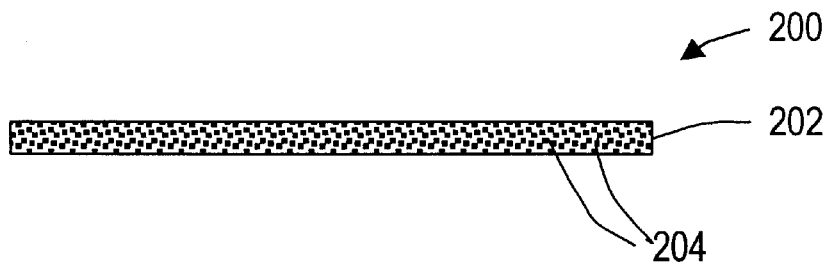
FIG. 2 shows a cross section of a magnetic sheet article of the invention.

The magnetic sheet material of the invention may be a single self-supporting layer of a flexible material containing magnetizable particles. Such an embodiment is illustrated in FIG. 2 which shows a magnetic layer 200 comprised of a matrix 202 having magnetic particles 204 dispersed throughout.

The magnetic particles used in the magnetic sheet of the invention may be any conventional particles used in the manufacture of flexible magnetic layers. Suitable particulate magnetic materials include essentially all known ferromagnetic or ferrimagnetic particles, e.g., $\gamma$-$Fe_2O_3$, $\gamma$-$Fe_3O_4$, which may be optionally doped with cobalt, chromium dioxide ($CrO_2$), ferromagnetic alloys such as Fe·Co, Fe·Ni, Fe.Ni.Zn, Fe.Co.Ni.Cr, neo iron, and the like, can be used. Magnetic particles with a high coercive field, such as strontium and barium ferrites, alloys with a base of aluminum, nickel, and cobalt (ALNICO), ceramic magnetic particles, etc., can be used. It is preferred to use particles of strontium ferrite.

The matrix for the magnetic particles may be any conventional coatable, extrudable, or curable natural or synthetic resin. For example, polyolefins, styrene-butadiene resins, natural and synthetic rubbers and the like can be used as binding matrices. The magnetic layer 202 comprising a thermoplastic matrix filled with magnetic particles preferably comprises from about 50 percent to about 95% by weight of magnetic particles based on the total weight of the sheet, more preferably from about 60 percent to about 90 percent by weight and most preferably from about 80 percent by weight to about 90 percent by weight. The thermoplastic matrix material comprises from about 5 percent to about 50 percent by weight of the magnetic layer, more preferably from about 10 percent to about 40 percent by weight thereof, and most preferably from about 10 percent to about 20 percent by weight thereof. Preferably the magnetic layer has a thickness of from about 15 mils (0.38 millimeters) to about 60 mils (1.52 millimeters), more preferably from about 20 mils (0.51 mm) to about 45 mils (1.14 mm), and most preferably from about 25 mils (0.64 mm) to about 35 mils (0.89 mm).

Figure 3:
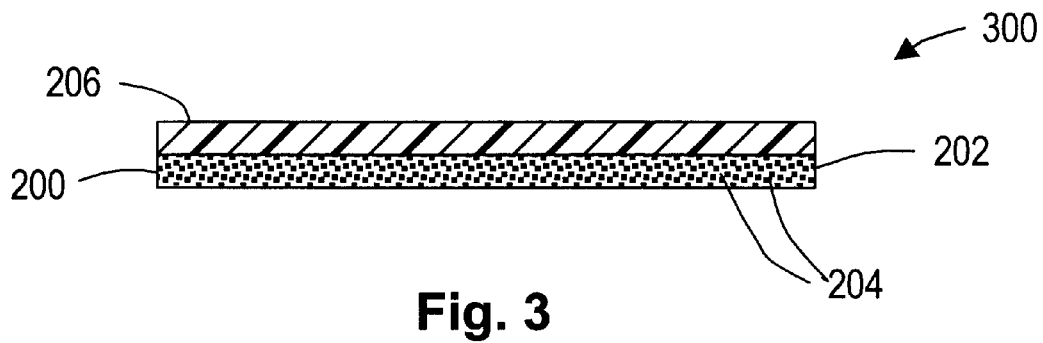
FIG. 3 shows a cross-section of an embodiment of the invention wherein the magnetic layer is supported on a flexible substrate.

The magnetic layer may be coated onto a supporting layer to provide greater strength and durability for greater convenience in handling and applying the material to the skin. Such an embodiment is shown in FIG. 3 wherein a magnetic sheet article 300 comprises a magnetic layer 200 having magnetic particles 204 dispersed in a matrix 202, the magnetic layer being coated on or bonded to a supporting layer 206 of synthetic resin, woven or nonwoven textile web, or the like. The magnetic article is preferably flexible in order to conform easily to the anatomical location to which it is applied. Accordingly, the supporting layer may be any material, preferably flexible, having sufficient strength to provide a sheet that can be handled and applied to the therapeutic site. When a supporting layer is used as a component of the magnetic sheet material, the magnetic layer itself may be made thin and need not be self-supporting.

Figure 4:
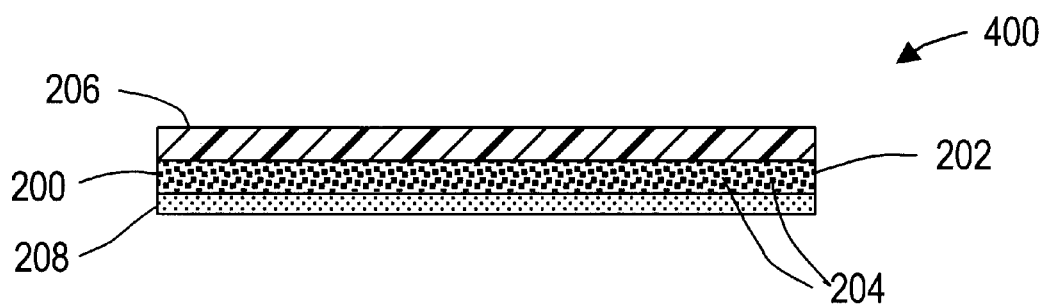
FIG. 4 shows a cross-section of an embodiment of the invention incorporating an adhesive layer for adhering the magnetic layer to the skin.

In order to assure a convenient application and close adherence of the magnetic sheet material to the skin, a layer of a physiologically acceptable adhesive may be applied to one major surface of the magnetic layer. Such an embodiment is shown in FIG. 4 wherein a magnetic sheet article 400 similar to the article 300 illustrated in FIG. 3 is additionally provided with a layer 208 of adhesive. The adhesive is preferably a low-tack adhesive that will hold the magnetic article of the invention firmly to the skin but will not adhere so strongly to the skin that removal of the magnetic layer is difficult or painful. Such adhesives are well known in the medical and cosmetic areas for use on various skin-adherent bandages, and the like. Any conventional adhesive used in surgical and/or cosmetic applications is suitable for such an adhesive layer.

Figure 5:
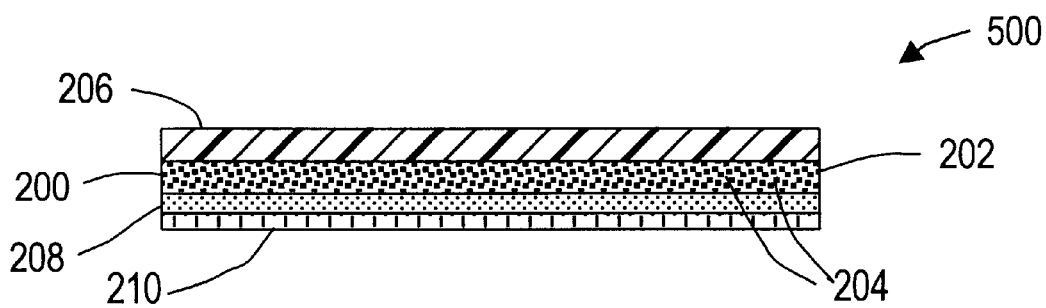
FIG. 5 shows a cross-section of the embodiment of FIG. 4 provided with a release layer covering the adhesive layer.

The adhesive layer may be further provided with a protective covering of a release layer for convenient storage and distribution. The release layer can then be removed immediately before the magnetic layer is applied, just as is commonly done with commercial bandages for minor wounds. FIG. 5 shows an embodiment 500 of the invention wherein the magnetic sheet is provided with such a covering layer 210 of a release material on the adhesive layer. The release liner 210 applied to the adhesive layer 208 may be of any conventional type. Silicone-coated paper is suitable, as well as webs of polyolefin such as polyethylene or polypropylene. The release layer is preferably a polyolefin. The release layer may have a thickness ranging from about 1 mil (25 micrometers) to about 16 mils (0.41 mm), more preferably from about 2 mils (51 micrometers) to about 5 mils (127 micrometers), and most preferably from about 3 mils (76 micrometers) to about 4 mils (102 micrometers). The release layer may have colored surface and/or may contain a colorant. The release layer is preferably free of magnetic powder and paramagnetic powder.

Figure 6:
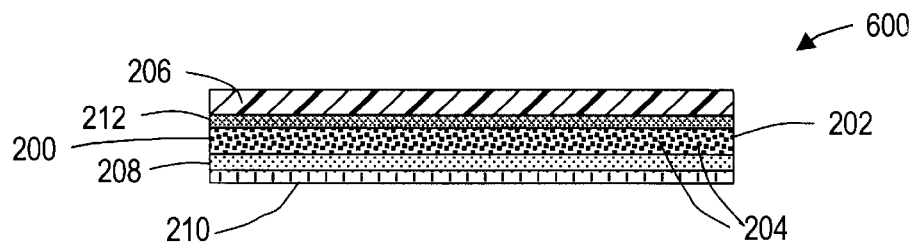
FIG. 6 shows a cross-section of an embodiment of the invention incorporating a magnetically permeable layer.

The magnetic sheet material of the invention may be provided with an auxiliary layer of a magnetically permeable material on the major surface opposite to the major surface closest to the skin. Such a magnetically permeable layer can enhance the strength of the magnetic field that permeates the region of the body to be treated. FIG. 6 illustrates an embodiment of the invention that includes a magnetically permeable layer 212. The magnetically permeable layer 212 can be a foil of a magnetically permeable metal such as iron or a ferromagnetic alloy or the like. The magnetically permeable layer 212 can also be a layer comprised of magnetic particles, preferably of a material that exhibits high permeability with low magnetic remanence, i.e., a so-called soft magnetic material, dispersed in a suitable binder. Suitable magnetic metal and ferrite particles are well known to those skilled in the art. The binders used for the particles in the magnetically permanent layer can be the same as used for the particles in the magnetic layer, and the proportions and ranges thereof can also be the same as set forth above for the magnetic layer.

Figure 7:
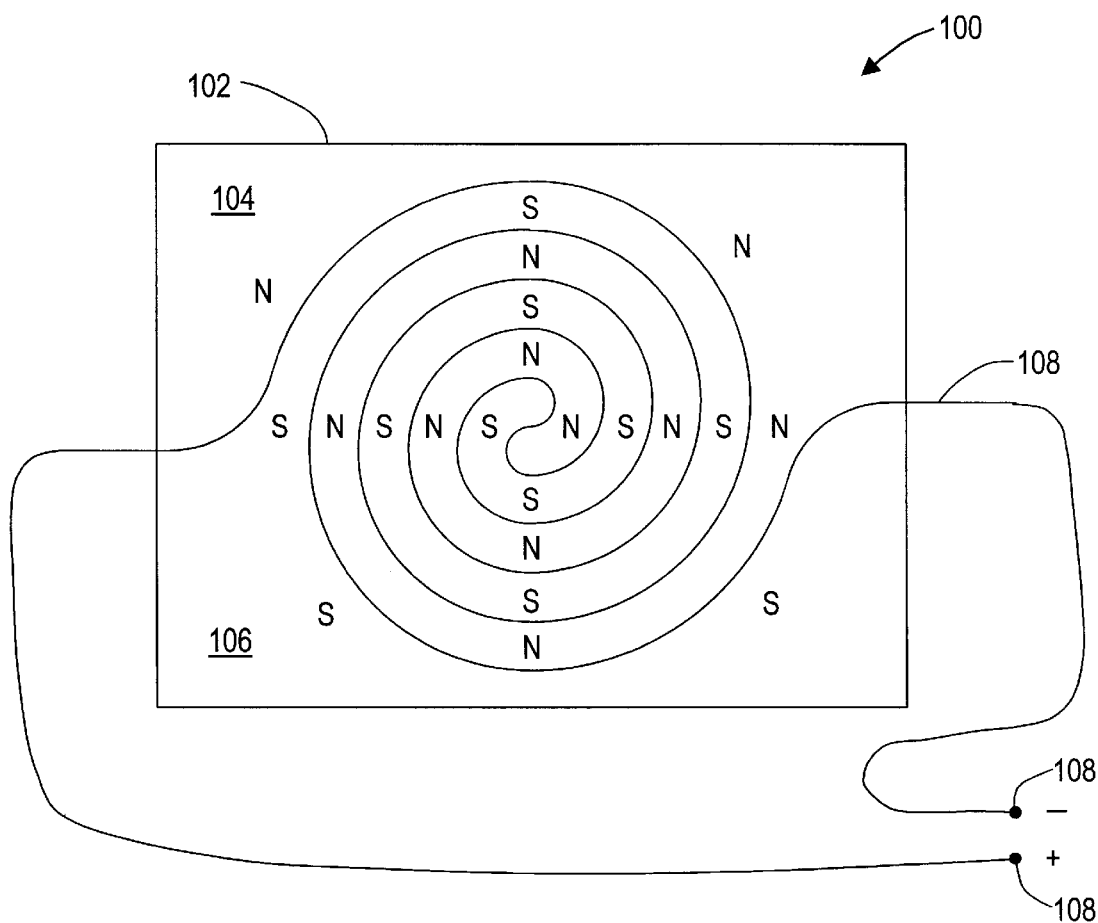
FIG. 7 is a schematic illustration of an arrangement for producing a spiral magnetic field in a sheet material of the invention.

The spirally magnetized sheet material of the invention can be prepared by any conventional procedure for preparing magnetic sheet materials. Magnetization or poling of the sheet can conveniently be performed by a pulse or discharge magnetizer, as illustrated in FIG. 7. A wire 108 is applied to the surface of the sheet to be magnetized in a spiral patter, e.g., as illustrated in the figure. A strong magnetizing field is then generated by passing a large current, e.g., about 6000 amperes, through the wire for a brief period of time, e.g., a few milliseconds. Such high current is applied by a conventional capacitive-discharge magnetizer connected at terminals 110 and 112.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

I claim:

1. A magnetic sheet material having at least one major surface magnetized in a direction generally normal to said surface comprising a single continuous area of north magnetic polarity alternating with a single continuous area of south magnetic polarity, at least a portion of said alternating areas of magnetic polarity being intertwined in a spiral pattern around a central point.

2. The magnetic sheet material of claim 1, comprised of magnetic particles dispersed in a flexible skin-compatible binder.

3. The magnetic sheet material of claim 1, having a first major surface and a second major surface wherein a flexible backing layer is adhered to said first major surface.

4. The magnetic sheet material of claim 3, wherein a layer of a skin-compatible pressure-sensitive adhesive is provided on said second major surface.

5. The magnetic sheet material of claim 4, wherein said adhesive layer is covered with a release liner.

6. The magnetic sheet material of claim 1, additionally comprising a layer of a magnetically permeable material adjacent to a major surface of said magnetic sheet material.

* * * * *